US010682132B2

(12) United States Patent
Bonutti

(10) Patent No.: US 10,682,132 B2
(45) Date of Patent: Jun. 16, 2020

(54) SYSTEM FOR MAGNETIC MOVEMENT OF TISSUE AND IMPLANTS

(71) Applicant: P Tech, LLC, Effingham, IL (US)

(72) Inventor: Peter M. Bonutti, Manalapan, FL (US)

(73) Assignee: P Tech, LLC, Effingham, IL (US)

( * ) Notice: Subject to any disclaimer, the term of this patent is extended or adjusted under 35 U.S.C. 154(b) by 254 days.

(21) Appl. No.: 15/682,816

(22) Filed: Aug. 22, 2017

(65) Prior Publication Data

US 2017/0347998 A1 Dec. 7, 2017

Related U.S. Application Data

(63) Continuation of application No. 10/784,401, filed on Feb. 23, 2004, now Pat. No. 9,770,238, which is a continuation of application No. 10/005,652, filed on Dec. 3, 2001, now Pat. No. 6,719,765.

(51) Int. Cl.
*A61B 17/04* (2006.01)
*A61N 1/378* (2006.01)
*A61B 34/20* (2016.01)

(52) U.S. Cl.
CPC .......... *A61B 17/0469* (2013.01); *A61B 17/04* (2013.01); *A61B 17/0401* (2013.01); *A61N 1/3787* (2013.01); *A61B 34/20* (2016.02); *A61B 2017/0414* (2013.01); *A61F 2210/009* (2013.01)

(58) Field of Classification Search
CPC . A61B 17/0469; A61B 17/04; A61B 17/0401; A61B 34/20; A61B 2017/0414; A61N 1/3787; A61F 2210/009

USPC ............................................ 606/153; 600/12
See application file for complete search history.

(56) References Cited

U.S. PATENT DOCUMENTS

| 5,201,744 A | * | 4/1993 | Jones | A61B 17/0469 606/1 |
| 5,395,033 A | * | 3/1995 | Byrne | A61B 17/07207 227/175.1 |
| 5,417,701 A | * | 5/1995 | Holmes | A61B 17/0469 606/147 |
| 5,431,670 A | * | 7/1995 | Holmes | A61B 17/0469 606/1 |
| 5,556,402 A | * | 9/1996 | Xu | A61B 17/0469 112/169 |
| 6,298,257 B1 | * | 10/2001 | Hall | A61B 5/06 600/407 |

(Continued)

*Primary Examiner* — Julian W Woo
(74) *Attorney, Agent, or Firm* — Stinson LLP

(57) ABSTRACT

The present invention relates to an instrument and method for passing a medical implement through tissue with magnetic forces. The implement can be an implant, either permanent or temporary, and is provided with a magnetic component. A magnetic field is established and the magnetic component and/or magnetic field is manipulated to drive the implant through tissue. Alternatively, the instrument itself is the implement and includes at least one magnetic element so that a magnetic field established by an external magnetic generator drives the instrument through tissue. In another embodiment, the instrument includes two magnetic elements that are moveable with respect to one another and interaction between the magnetic elements drives the instrument through the tissue. Examples of applications of the present invention include a suture passer and a tissue anchor.

12 Claims, 6 Drawing Sheets

(56) References Cited

U.S. PATENT DOCUMENTS

| | | | | |
|---|---|---|---|---|
| 6,315,709 | B1 * | 11/2001 | Garibaldi | A61B 17/12022 600/12 |
| 6,364,823 | B1 * | 4/2002 | Garibaldi | A61B 17/12022 600/12 |
| 6,459,924 | B1 * | 10/2002 | Creighton, IV | A61B 1/00158 128/899 |
| 8,900,293 | B2 * | 12/2014 | Forbes | A61F 2/82 600/12 |
| 2002/0087177 | A1 * | 7/2002 | Wallace | A61B 17/12022 606/157 |

* cited by examiner

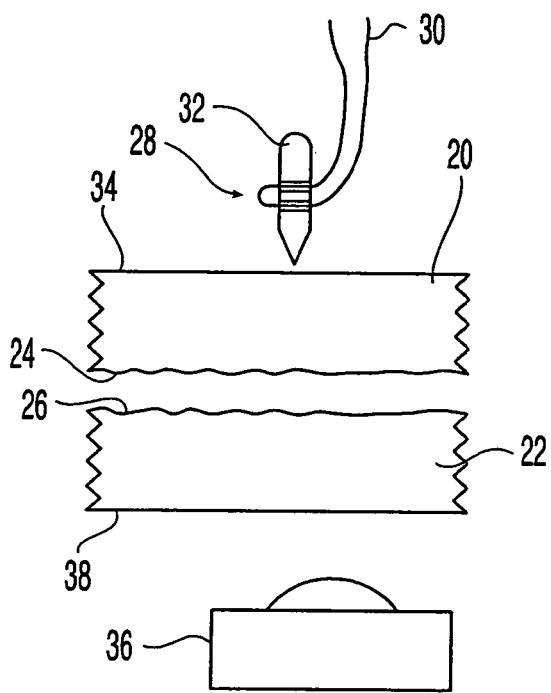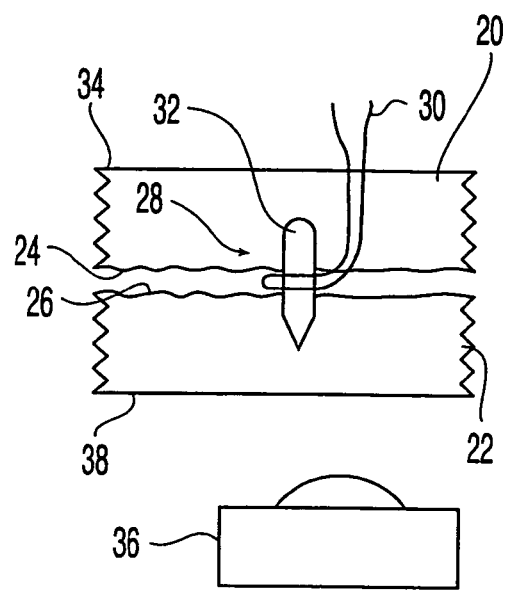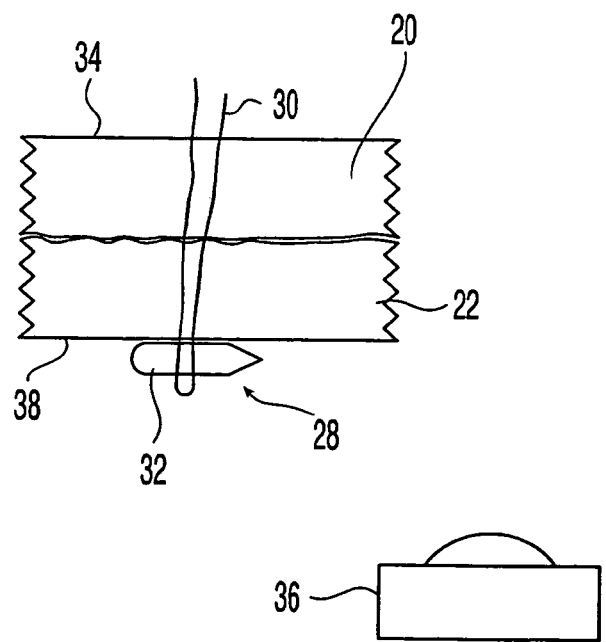
Fig. 1  Fig. 2
Fig. 3

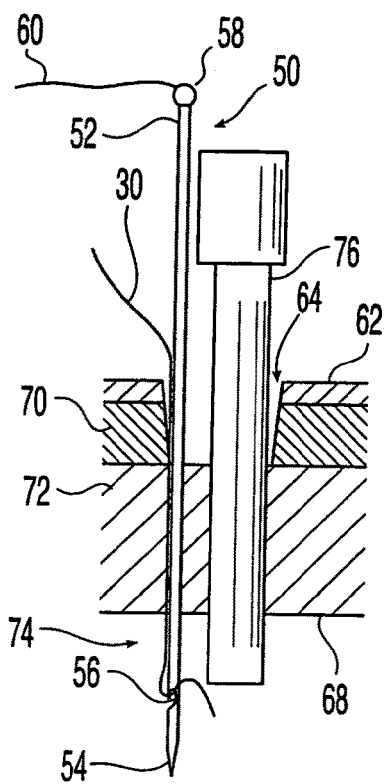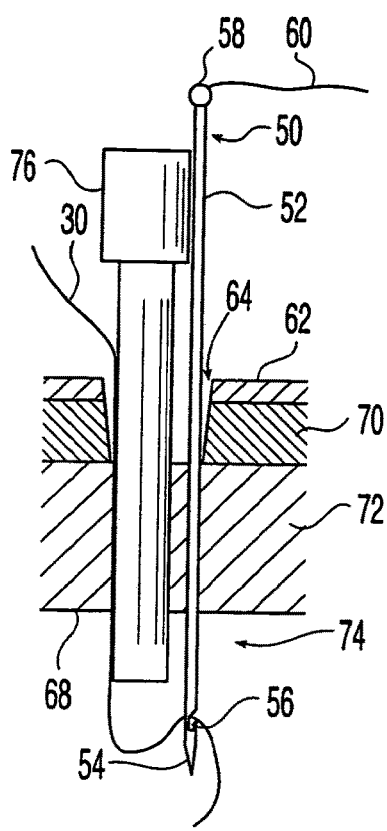
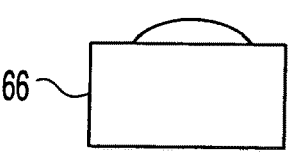
Fig. 4              Fig. 5
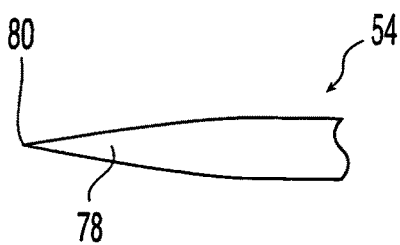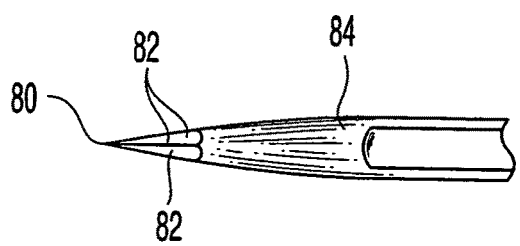
Fig. 6              Fig. 7
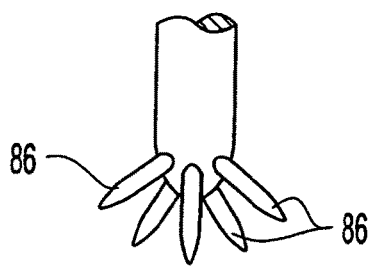
Fig. 8

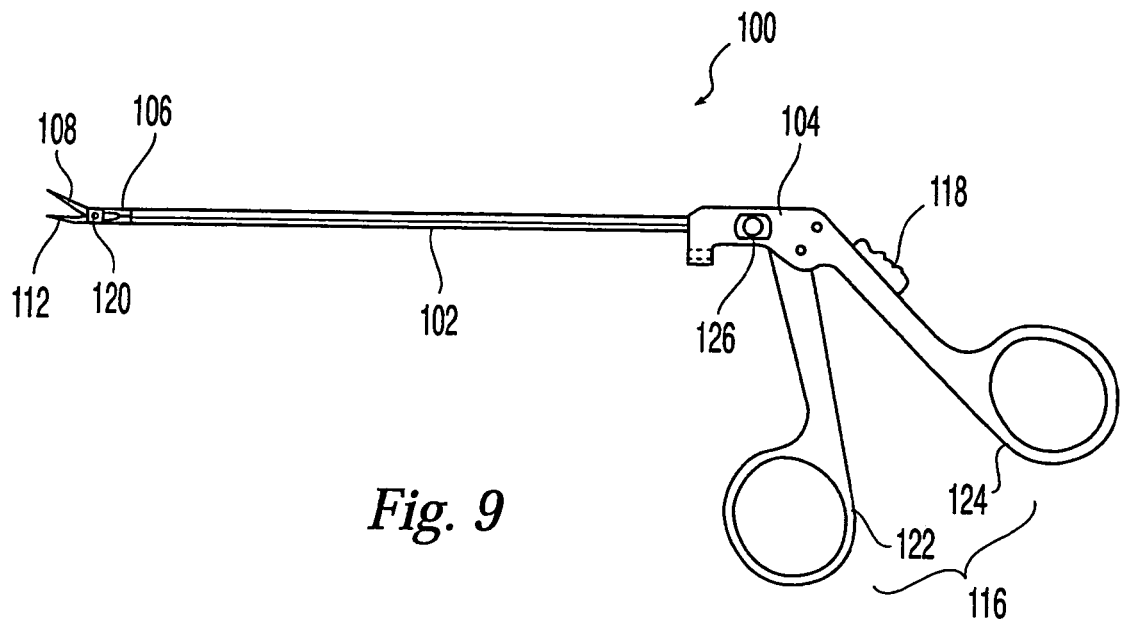
Fig. 9
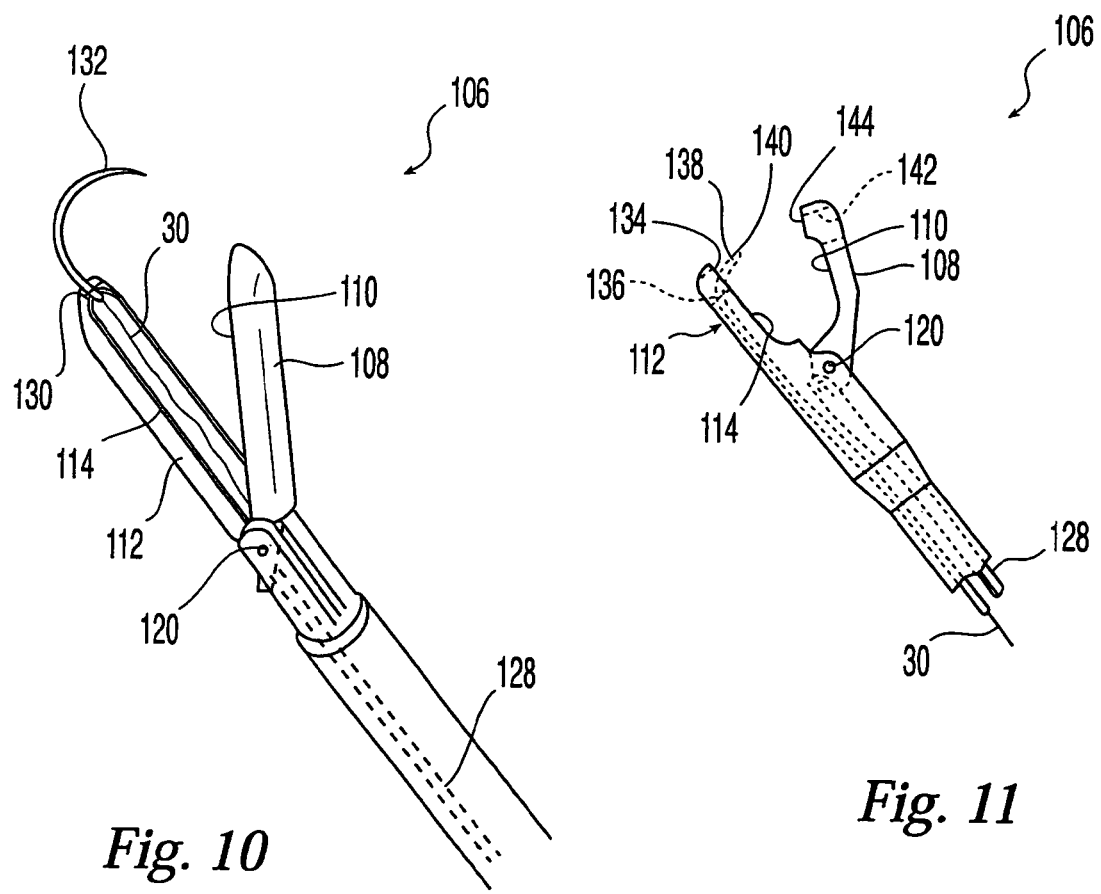
Fig. 10
Fig. 11

SYSTEM FOR MAGNETIC MOVEMENT OF TISSUE AND IMPLANTS

CROSS-REFERENCE TO RELATED APPLICATION

This application is a continuation of U.S. patent application Ser. No. 10/784,401, filed on Feb. 23, 2004 (now U.S. Pat. No. 9,770,238), which in turn is a continuation of U.S. patent application Ser. No. 10/005,652, filed on Dec. 3, 2001 (now U.S. Pat. No. 6,719,765).

FIELD OF THE INVENTION

The present invention relates to an instrument and method for passing a medical implement, such as suture or similar element, through tissue.

BACKGROUND OF THE INVENTION

The insertion of a medical instrument or implant through tissue can involve the application of significant mechanical force. For example, the insertion of a suture through thick connective tissue requires substantial pressure, regardless of whether the suture is pushed or pulled through the tissue. In an open surgical procedure, the exposure of the large surgical incision provides access for manipulation and visualization. Nevertheless, insertion can still be problematic. Furthermore, it is often desirable to minimize the size of this incision to reduce scarring and soft tissuetrauma.

Arthroscopy and other minimally invasive surgical procedures utilize small incisions or portals for insertion of diagnostic and surgical instruments manipulated externally of the body, and therefore, avoid the trauma associated with large incisions as well as the hospitalization and prolonged recovery periods required with open surgery. While it is not always required, an endoscope may be used to enhance visualization. However, due to the small surgical incision of these minimally invasive approaches, it is frequently difficult to gain the access required to insert and manipulate the instrument or implant. Remotely passing a suture through tissue can be one particularly troublesometask.

The prior art teaches a number of devices attempting to solve this problem. For example, the Carter-Thomason suture passer disclosed in U.S. Pat. No. 5,496,335 has a sharp tip that opens and closes so that the tip can both grasp the suture and penetrate through tissue. However, this instrument, like most, if not all, relies solely on mechanical force to pass the suture through tissue.

Thus, there exists a need for an improved suture inserter and method.

SUMMARY OF THE INVENTION

The present invention relates to a method of passing a medical implement having a magnetic component through tissue. The medical implement is placed on a first side of the tissue, a magnetic field is established on a second side of the tissue, and at least one of the magnetic component and magnetic field is manipulated to drive the medical implement through the tissue. In one embodiment, the magnetic component is a portion of the medical implement. Alternatively, the magnetic component can be attached to the medical implement.

The magnetic component can be made of a magnetizable material, or can actually be a magnet, either a permanent magnet or an electromagnet. Regardless of the nature of the magnetic component, the magnetic field location can be altered to provide directional control of the medical implement as it is driven through the tissue. In an exemplary embodiment, the medical implement is made of a non-magnetic matrix and the magnetic component is dispersed within the matrix material. The matrix can be a resorbable material, with the magnetic component comprising a plurality of iron particles.

The present invention also relates to a surgical instrument for delivery of an implant through tissue. The implant has a body, a carrier located on the body forremoveably securing at least a portion of the implant to the instrument, a tip located at a distal end of the body and configured and dimensioned for insertion through the tissue, and a magnetic element located on the body. Interaction between the magnetic element and a magnetic field external to the tissue drives the instrument through the tissue.

The magnetic element can be part of the body or attached to the body. The magnetic element can be a permanent magnet or an electromagnet. Regardless, the magnetic element can be movable to provide directional control of the instrument as it is driven through the tissue.

The invention also related to a suture passer for inserting a suture through tissue. The suture passer includes an elongate body having proximal and distal ends, a first jaw disposed on the distal end of the body and having a first magnetic element, and a second jaw disposed on the distal end of the body and having a second magnetic element. At least one of the first and second magnetic elements is an electromagnet and the other can be made of a magnetizable material. A handle is disposed on the proximal end of the body for manipulation of the suture passer and a controller is provided for operating the electromagnet. The first and second jaws are movable relative to each other from a closed position to an open position and one of the polarity and strength of the electromagnet is changed to move the first and second jaws to the open andclosed positions.

In one embodiment, the first jaw has a piercer for penetrating the tissue and the second jaw has an opening for receiving the piercer. The handle can be operated to move the first and second jaws to the open and closed positions. The piercer can be provided with an opening for receiving the suture so that the suture can be passed through the tissue after the piercer has penetrated the tissue. In an exemplary embodiment, the first magnetic element is the piercer and the first and second jaws are slideable with respect to one another to vary the angle the piercer is inserted through the tissue.

In another embodiment, the first jaw has a clip for holding a sutureneedle. Again, the handle can be operated to move the first and second jaws to the open and closed positions.

Both the first and second magnetic elements can be electromagnets. Accordingly, the first and second electromagnets can be selectively activatable and deactivatable to move an implant back and forth through tissue. A mechanical stop can be provided on either or both of the jaws to removeably secure the implant to the jaw. The mechanical stop can be either independent of the controller for the electromagnet or can be operated by the controller.

In use, a suture needle, with suture attached thereto, is removeably secured to the first jaw of the suture passer. A portion of the body of the suture passer is inserted through an incision in a patient so that the first and second jaws are located adjacent the tissue. The first and second jaws are separated to the open position so that the first jaw is on a first side of the tissue and the second jaw is on a second side of the tissue and the controller is operated to move the first and second jaws to the closed position so that the needle tip penetrates the tissue. After the needle penetrates the tissue, the needle can be released from the first jaw; and pulled through to thereby pass the suture through the tissue. If desired, the needle can be removeably secured to the second jaw to pass the needle back and forth through the tissue.

The suture passer can also be used by providing the first jaw with a piercer for penetrating the tissue and providing the second jaw with an opening for receiving the piercer. At least a portion of the body of the suture passer is inserted through an incision in a patient so that the first and second jaws are located adjacent the tissue. The first and second jaws are separated to the open position so that the first jaw is on a first side of the tissue and the second jaw is on a second side of the tissue. The controller is operated to move the first and second jaws to the closed position so that the tip penetrates the tissue. The suture is then fed through a bore in the piercer.

BRIEF DESCRIPTION OF THE DRAWINGS

Preferred features of the present invention are disclosed in the accompanying drawings, wherein similar reference characters denote similar elements throughout the several views, and wherein:

FIG. 1 schematically shows an embodiment of the present invention, in the form of a suture anchor and an external magnetic field generator, prior to insertion in first and second tissue sections;

FIG. 2 shows the suture anchor of FIG. 1 inserted between first and second tissue sections;

FIG. 3 shows the suture anchor of FIG. 1 completely inserted through the second tissue section;

FIG. 4 schematically shows another embodiment of the present invention, in the form of a suture passer and an external magnetic field generator, inserted in the tissue at a first location;

FIG. 5 shows the suture passer of FIG. 4 re-inserted in the tissue at a second location;

FIG. 6 shows one embodiment of a tip for penetrating tissue;

FIG. 7 shows another embodiment of a tip for penetrating tissue;

FIG. 8 shows another embodiment of a tip for penetrating tissue;

FIG. 9 shows another embodiment of the present invention, in the form of a suture passer;

FIG. 10 shows one embodiment of for the suture passer of FIG. 9;

FIG. 11 shows another embodiment of for the suture passer of FIG. 9;

DETAILED DESCRIPTION OF THE INVENTION

Figure 12:
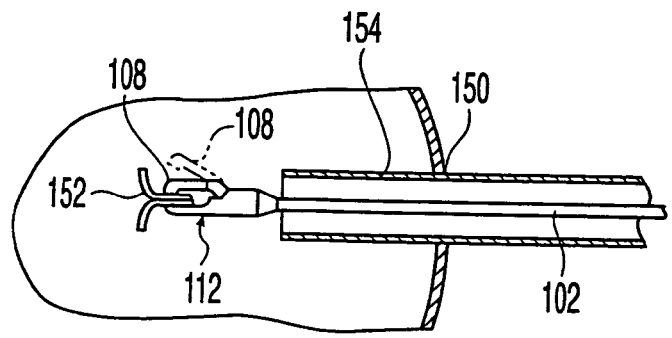
FIG. 12 shows the suture passer of FIG. 9 clamping the tissue to be sutured.
Figure 13:
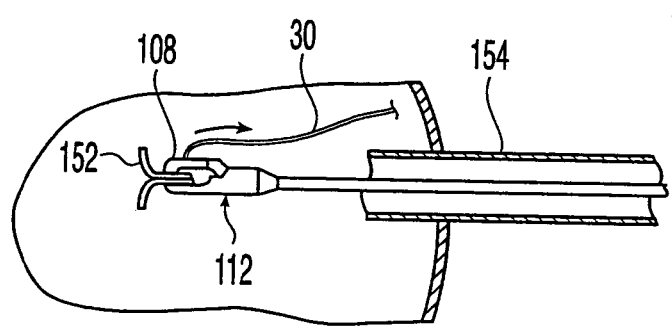
FIG. 13 shows the suture passer of FIG. 9 after the suture has passed through the tissue.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto. Finally, any reference to a particular biological application, such as fixation with a suture anchor, is simply used for convenience as one example of a possible use for the invention and is not intended to limit the scope of the present invention thereto.

FIGS. 1-3 schematically show one embodiment of the present invention. First and second tissue sections 20, 22 are to be brought into close apposition. Specifically, surface 24 of first tissue section 20 and surface 26 of second tissue section 22 are to be placed in contact. A medical implement, in the form of a suture anchor 28 is provided in this regard. Suture anchor 28 can be used in a wide variety of applications including rotator cuff repair, heart valve replacement and repair, vessel repair and replacement, hernia repair, anastomosis, and other procedures.

Suture anchor 28 includes a flexible suture 30 so that in order to join first and second tissue sections 20, 22, suture anchor 28 passes from first tissue section 20 through second tissue section 22 with suture 30 extending across surfaces 24, 26. Suture 30 is then pulled tight to draw surfaces 24, 26 into contact and a knot or other tension retaining mechanism keeps surfaces 24, 26 in contact. Examples of methods and apparatuses for securing suture that can be used are taught in U.S. Pat. No. 6,231,592 B1, the contents of which are incorporated herein by reference. A transducer or other tension-measuring device can be used to monitor and/or control the tension on the suture.

Under the prior art, mechanical forces are used to either push or pull suture anchor 28 from first tissue section 20 through second tissue section 22. With the present invention, suture anchor 28 is provided with a magnetic component 32. Magnetic component 32 can be a portion of suture anchor 28. Alternatively, magnetic component 32 can be permanently or removeably attached to suture anchor 28. Magnetic component 32 can be made of any magnetizable material. If the surgical implement is intended to be an implant, like suture anchor 28, magnetic component 32 should be a biocompatible material. Magnetic component 32 can be a permanent magnet, or, as discussed in more detail below with respect to FIGS. 4-6, magnetic component can be an electromagnet. Examples of permanent magnets include ferromagnetic materials such as iron, nickel, and cobalt.

In use, suture anchor 28 is placed on a first side 34 of first tissue section 20 and a magnetic field generator 36 is placed on a second side 38 of second tissue section 22. In one embodiment, magnetic field generator 36 is a permanent magnet so that the magnetic field with respect to suture anchor 28 can be varied by changing the location and orientation of the permanent magnet. In another embodiment, magnetic field generator 36 is an electromagnet and is provided with a controller for electronically varying the generated electric field. Thus, regardless of the exact nature of magnetic component 32 and magnetic field generator 36 (i.e. permanent or electromagnetic), the respective magnetic fields can be manipulated. Such manipulation can be as simple as changing the relative locations of magnetic component 32 and magnetic field generator 36 or turning the current on to the electromagnet.

As shown in FIG. 2, the magnetic attraction between magnetic component 32 of suture anchor 28 and the magnetic field of magnetic field generator 36 drives suture anchor 28 through first and second tissue sections 20, 22. Although it is envisioned that the magnetic attraction alone could drive suture anchor 28 through first and second tissue sections 20, 22, this magnetic attraction could be assisted by mechanical force, e.g. pushing or pulling suture anchor 28 in addition to the magnetic field. The desirability of this assistance will depend upon a number of factors including surgeon preference, tissue type, tissue thickness, and other similar considerations. Furthermore, it is also possible to create an optional passageway (e.g. a cannula, pre-drilling, etc.) for suture anchor 28. The cross-sectional size and depth of the passageway can be determined by the surgeon.

In addition to driving suture anchor 28, the magnetic field interactions can be used to provide directional control of suture anchor 28. An example of such control is shown in FIG. 3. Suture anchor 28 has completely penetrated second tissue section 22 and magnetic field generator 36 has been moved. This causes suture anchor 28 to turn with its longest dimension resting against second tissue section 22. If magnetic field generator 36 is moved from second side 38 to first side 34, suture anchor 28 will be driven back from second tissue section 22 through first tissue section 20. In this fashion, suture anchor 28 can be repeatedly moved across first and second tissue sections 20, 22 to thereby provide multiple suture stitches. If magnetic component 32 is a permanent magnet or electromagnet, an analogous effect of moving the surgical implement back and forth through tissue can be achieved by reversing the polarity of magnetic component 32.

As shown in FIGS. 1-3, both first and second sides 34, 38 appear readily accessible. However, it should be noted that first and second tissue sections 20, 22 can be internal tissues with intervening tissue layers such that first and second sides 34, 38 are not exposed, except for any access ports or incisions created by the surgeon.

As previously noted, magnetic component 32 can be a part of suture anchor 28. In an exemplary embodiment, suture anchor 28 is made of a non-magnetizable matrix and magnetic component 32 is dispersed within the matrix. One particularly suitable class of matrix materials is resorbable materials such as poly-lactide acid, poly-glycolic acid, combinations thereof, and other similar substances. In such cases, magnetic component 32 can be made of particles, such as iron, that are well tolerated by the body and can be removed from the body by normal physiological mechanisms, e.g. through urination, perspiration, and other excretion processes. As the matrix dissolves, the particles are naturally removed from the body with no adverse effects.

Although FIGS. 1-3 show the method according to the present invention used with a suture anchor, the method can be used with any implant that passes through tissue. Furthermore, the method can also be used with any medical instrument that passes through tissue. FIGS. 4 and 5 schematically show one such instrument.

Instrument 50 is a suture passer, used to pass a suture through tissue. Instrument 50 includes an elongate body 52 with a tip 54 located at a distal end. Tip 54 is configured and dimensioned for insertion through the tissue. Body 52 has a carrier 56 for removeably securing at least a portion of suture 30 to suture passer 50. As shown, suture carrier 56 is a slot. However, suture carrier can be other suitable mechanisms for temporally coupling the implant, in this case suture 30 to suture passer 50. Other mechanisms include an eyelet or a barb.

A magnetic element 58 is located on body 52. Magnetic element 58 can either be a part of body 52 or can be attached to body 52. As shown, magnetic element 58 is an electromagnet and wiring 60 connects the electromagnet to a power supply and controller. In use, suture 30 is connected to suture passer 50 and suture passer 50 is positioned on a first side 62 of the desired insertion site 64. An external magnetic field generator 66 is located on a second side 68 of insertion site 64. In one embodiment, magnetic field generator 66 is a permanent magnet so that the magnetic field with respect to suture passer 50 can be varied by changing the location and orientation of the permanent magnet. In another embodiment, magnetic field generator 66 is an electromagnet and is provided with a controller for electronically varying the generated electric field. Thus, regardless of the exact nature of magnetic component 58 and magnetic field generator 66 (i.e. permanent or electromagnetic), the respective magnetic fields can be manipulated. Such manipulation can be as simple as changing the relative locations of magnetic component 58 and magnetic field generator 66 or turning the current on to the electromagnet.

The magnetic attraction between magnetic component 58 of suture passer 50 and the magnetic field of magnetic field generator 66 drives suture passer 50 through skin tissue 70 and internal tissue 72 and into internal cavity 74. A trochar 76, which is ordinarily in place for percutaneous surgeries, can be used to monitor the insertion. Although it is envisioned that the magnetic attraction alone could drive suture passer 50 from first side 62 to second side 68, this magnetic attraction could be assisted by mechanical force, e.g. pushing or pulling suture passer 50 in addition to the magnetic field. The desirability of this assistance will depend upon a number of factors including surgeon preference, tissue type, tissue thickness, and other similar considerations. Furthermore, it is also possible to pre-drill an optional passageway for suture passer 50. The cross-sectional size and depth of the passageway can be determined by the surgeon.

In addition to driving suture passer 50, the magnetic field interactions can be used to provide directional control of suture passer 50. For example, the polarity of magnetic element 58 or magnetic field generator 66 can be reversed to back suture passer 50 out of internal cavity 74. Accordingly, suture 30 is uncoupled from suture passer 50; suture passer 50 is removed and re-inserted at a second location. Suture 30 is recaptured with carrier 56 and suture passer 50 is again backed out of internal cavity 74 so that both ends of suture 30 are now exposed. Suture 30 can be knotted or otherwise secured to close the insertion site.

Although FIGS. 4 and 5 show elongate body 52 extending through skin and internal tissues 70, 72, the length of elongate body 52 can be selected for a given application. For example, elongate body 52 can have a length similar to that of a conventional suture needle. Given such a length, suture passer 50 can go through the tissue in any direction and angle, dependent upon wherever guided by the magnet. Regardless of the length of elongate body 52, tip 54 can be provided with a wide variety of geometries. FIG. 6 shows a tip 54 with a conical body 78 extending to a sharp end 80. FIG. 7 shows another embodiment of a tip with beveled edges 82. Ribs 84 can be provided to facilitate insertion through tissue. FIG. 8 shows a tip that is shaped like a mace and has multiple protrusions 86 extending from its distal end. The arrangement of multiple protrusions 86 is particularly useful in allowing suture passer 50 to travel in a variety of directions.

FIG. 9 shows another embodiment of the present invention. A suture passer 100 has an elongate body 102 with proximal and distal ends 104, 106. A first jaw 108 is disposed on distal end 106 of body 102 and has a first magnetic element 110. A second jaw 112 is also disposed on distal end 106 of body 102 and has a second magnetic element 114. As previously noted with respect to the other embodiments, either or both of first and second magnetic elements 110, 114 can be a magnet or a magnetizable material. In the exemplary embodiment shown in FIG. 9, one of the magnetic elements, first magnetic element 110, is an electromagnet and second magnetic element 114 is made of a magnetizable material. This arrangement could be reversed so that second magnetic element 114 is the electromagnet and first magnetic element 110 is made of the magnetizable material. Alternatively, both first and second magnetic elements 110, 114 are electromagnets.

A handle 116 is disposed on proximal end 104 of body 102 for manipulation of suture passer 100. A controller 118 is used to control the electromagnet. If both magnetic elements 110, 114 are electromagnets, controller 118 can be configured to control both or, alternatively, a second controller can be provided. Examples of suitable controllers include a push button to simply turn the electromagnet on and off, a three way switch to turn the electromagnet on and off and control the polarity, and a three way switch with a variable resistor so the polarity and strength of the electromagnet can be adjusted. The electronic circuitry for the electromagnet is well known to those of ordinary skill of the art and can be either partially or completely location on or within suture passer 100. If any portion of the circuitry is not on suture passer 100, wiring can connect this portion to the circuitry on suture passer 100.

A pivot point 120 pivotably couples one or both of first and second jaws 108, 112 to distal end 106 of body 102 so that first and second jaws 108, 112 are moveable with respect to one another. In particular, first and second jaws 108, 112 are moveable relative to each other from a closed position, with first and second jaws 108, 112 substantially in contact if there is nothing in between first and second jaws 108, 112, to an open position, with first and second jaws 108, 112 separated from each other. An optional spring or other biasing member can be used to bias first and second jaws 108, 112 in the open or closed position.

In use, the polarity and/or strength of the electromagnet is controlled to move first and second jaws 108, 112 between the open and closed positions. For example, if second magnetic element 114 is a permanent magnet, the polarity of first magnetic element 110 can be such that there is magnetic attraction between first and second magnetic elements 110, 114 so that first and second jaws 108, 112 are in the closed position. If the polarity is changed, there is a magnetic repulsion between first and second magnetic elements 110, 114 so that first and second jaws 108, 112 are in the open position. If second magnetic element 114 is not a permanent magnet, but is rather a magnetizable element, then merely turning on the electromagnet will move first and second jaws 108, 112 to the closed position. As previously noted, a spring or other biasing member can be used to bias first and second jaws 108, 112 in the closed position so that when the electromagnet is turned off, or sufficiently reduced in magnetic strength, first and second jaws 108, 112 move from the open to the closed position.

In an exemplary embodiment, handle 116 comprises first and second handles 122, 124, which are moveable with respect to each other and are operatively associated with first and second jaws 108, 112 so that movement of first and second handles 122, 124 moves first and second jaws 108, 112 between the open and closed positions. As shown, first and second handles 122, 124 are scissors-type handles, with first handle 122 rotatable toward second handle 124 about pivot point 126. First handle 122 is coupled to an end of an actuation rod 128. As best seen in FIGS. 10 and 11, the other end of actuation rod 128 is coupled to first jaw 108 so that squeezing of first and second handles 122, 124 results in axial movement of actuation rod 128 and, consequently, pivoting of first jaw 108 with respect to second jaw 112. Other handle mechanisms used for arthroscopic type instruments can be used. For example, U.S. Pat. No. 5,899,911, the contents of which are incorporated herein by reference, teaches a syringe-type handle and could be utilized on suture passer 100.

FIG. 10 also shows that second jaw 112 includes a clip 130 for holding suture needle 132. Suture 30 extends from suture needle 132 either along or within body 102. Alternatively, clip 130 can be located on first jaw 108. Other suitable retaining mechanisms for removeably securing needle 132 to one of first and second jaws 108, 112 can be used. U.S. Pat. No. 5,947,982, the contents of which are incorporated herein by reference, discloses jaw members capable of holding the needle so that the angular orientation of the needle can be varied. The use of such jaw members with suture passer 100 is also envisioned by the present invention.

FIG. 11 shows another embodiment of first and second jaws 108, 112. Second jaw 112 includes a wall 134 for engaging tissue to be sutured and a recess 136 in which is secured a hollow, tubular needle 138 having a cutting tip 140 to penetrate tissue to be sutured. Needle 138 can be curved such that the portion terminating at tip 140 extends substantially transverse from a portion of needle 138 secured in recess 136 and, thus extends substantially transverse from the plane of the ends of wall 134 of second jaw 112. First jaw 108 includes an aperture 142 therethrough aligned with needle 138 such that needle tip 140 will extend into the aperture when first and second jaws 108, 112 are closed. First jaw 108 has a surface 144 facing the surface of wall 134 of second jaw 112 such that tissue to be sutured can be clamped between surfaces 134 and 144 when first and second jaws 108, 112 are in the closed position.

As needle 138 is hollow, suture 30 can be fed therethrough, with the suture extending along or within body 30. Any number of known suture feed mechanisms can be used. An example of such a mechanism is taught by U.S. Pat. No. 4,957,498, the contents of which are incorporated herein by reference.

Use and operation of suture passer 100 will be described with reference to FIGS. 12-15. Suture passer 100 is inserted into the body through an incision or portal 150 in the skin and moved to tissue 152, which is to be sutured. Suture passer can be inserted through cannula 154 or suture passer 100 can be provided with a sharp tip to avoid the use of a cannula. Regardless, positioning of suture passer 100 can be monitored using conventional arthroscopic instruments that permit video viewing of the surgical site for inspection, diagnosis and surgery.

First and second jaws 108, 112 are moved to the open position by switching controller 118 to the appropriate position. This position can be such that first magnetic element 110, i.e. the electromagnet, is shut off so that first and second jaws 108, 112 swing open under the influence of a spring or other biasing member. Alternatively, controller 118 can be set in a position that causes the polarity of first magnetic element 110 to be such that magnetic repulsion between first and second magnetic elements 110, 114 causes first and second jaws 108, 112 to swing open. First and second jaws 108, 112 can also be opened by operating the conventional mechanism of first and second handles 122, 124. When first and second jaws 108, 112 are positioned on opposite sides of tissue 152, controller 118 is switched into a position such that magnetic attraction between first and second magnetic elements 110, 114 causes first and second jaws 108, 112 to move to the closed position. Tissue engaging surfaces 134 and 144 of first and second jaws 108, 112 clamp tissue 152 while needle 138 is forced through tissue 152 and into opening 142. Accordingly, suture passer 100 operates as a punch as needle 138 penetrates through tissue 152.

Although it is envisioned that the magnetic attraction alone could drive needle 138 through tissue 152, this magnetic attraction could be assisted by mechanical force, e.g. operating first and second handles 122, 124 to move first and second jaws 108, 112 toward the closed position. As previously noted, the desirability of this assistance depends upon a number of factors.

Figure 14:
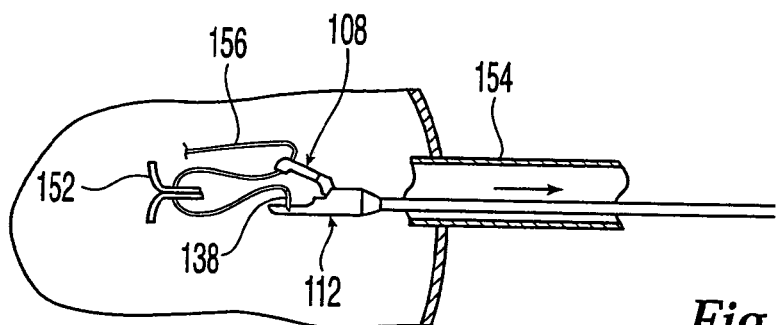
FIG. 14 shows the suture passer of FIG. 9 being withdrawn from the body.
Figure 15:
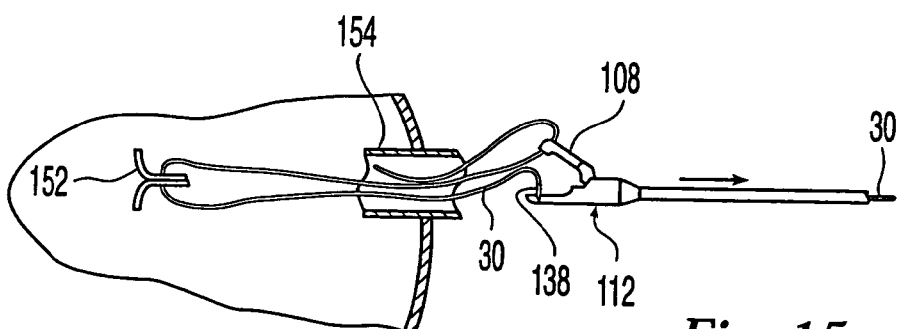
FIG. 15 shows the suture passer of FIG. 9 withdrawn from the body.

After first and second jaws 108, 112 are operated to punch needle 138 through tissue 152, suture 30 is forced through needle 138 to exit from tip 140 of needle 138 and pass through opening 142 in second jaw 112. Once a sufficient length of suture 30 material is fed through as shown in FIG. 14, first and second jaws 108, 112 are opened (either using controller 118 or handles 122, 124) to withdraw needle 138 back through tissue 152. Suture passer 100 is then moved away from tissue 152 causing a free end segment 156 of suture 30 to be folded back on itself with the edge of aperture 142 in second jaw 112 catching suture 30 to pull free end segment 156 out so that suture passer 100 can be withdrawn from the body leaving suture 30 in place through tissue 152 as shown in FIG. 15. With the ends of suture 30 outside the body, the surgeon in any conventional fashion can tie a knot, or other securing mechanisms can be used.

Figure 16:
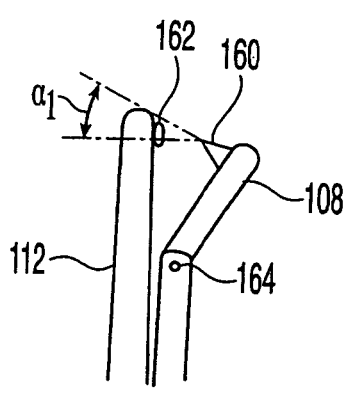
FIG. 16 shows another embodiment of jaws for the suture passer of FIG. 9.
Figure 17:
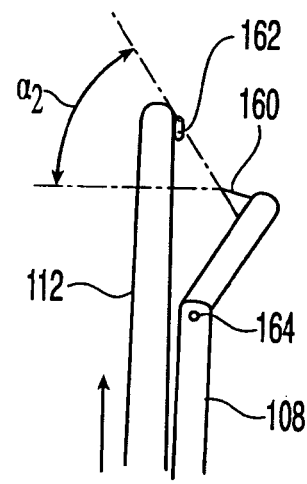
FIG. 17 shows the jaws of FIG. 16 with one jaw longitudinally moved with respect to the other jaw.

FIGS. 16 and 17 show another embodiment of first and second jaws 108, 112. First and second jaws 108, 112 are longitudinally moveable with respect to one another so that the angle at which needle 160 is inserted through the tissue can be varied. As shown in FIG. 16, magnetic element 162 on second jaw 112 lines up with needle 160 so that needle 160 would be inserted at an angle a1 that is close to zero degrees. In other words, needle 160 would enter the tissue substantially perpendicular to the plane of the tissue. In FIG. 17, first and second jaws 108, 112 have been moved with respect to one another so that magnetic element 162 would attract needle 160 to be inserted at an angle a2 that is greater than a1.

There are a number of different mechanisms to achieve relative longitudinal movement of first and second jaws 108, 112. For example, first jaw 108 can be provided with a pivot point 164 to effect movement of first and second jaws 108, 112 between the open and closed positions. This allows second jaw 112 to be moveable with respect to first jaw 108 without hindering opening and closing of first and second jaws 108, 112. This movement of second jaw 112 can be controlled with any known means located on the body of the suture passer.

Figure 18:
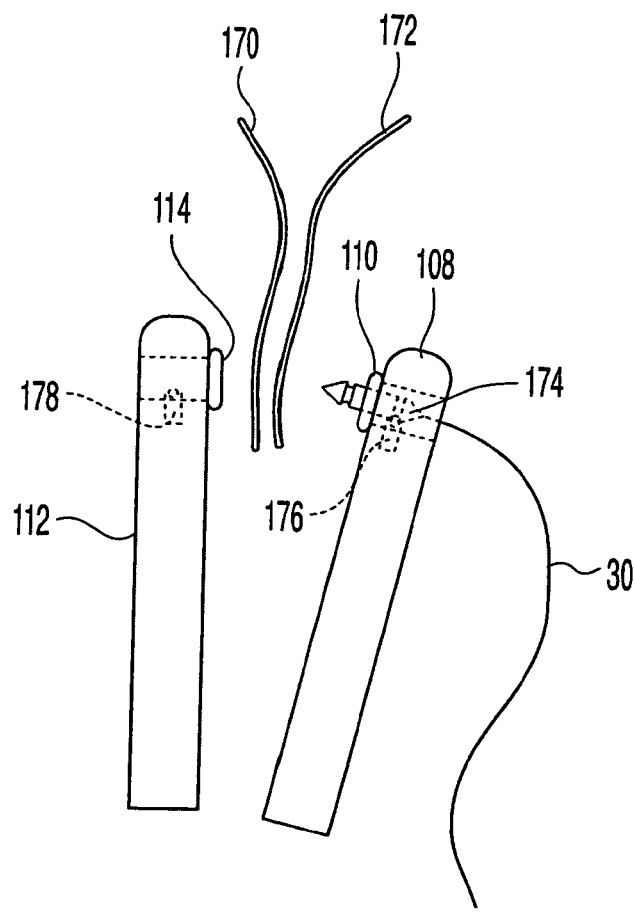
FIG. 18 shows another embodiment of for the suture passer of FIG. 9.

In the embodiment of FIG. 18, both first magnetic element 110 on first jaw 108 and second magnetic element 114 on second jaw 112 are magnets. As first and second jaws 108, 112 are positioned to be proximal to tissue sections 170, 172, first magnetic element 110 is activated so that implant 174 is attached to first jaw 108. Although the magnetic interaction between first magnetic element 110 and implant 174 may be sufficient to secure implant 174 to first jaw 108, first jaw 108 can be provided with a mechanical stop 176 to further secure implant 174 to first jaw 108. Mechanical stop 176 is shown as a ball detent mechanism that automatically activates when implant 174 is inserted. However, mechanical stop 176 can be configured to activate when first magnetic element 110 is activated, or a separate triggering mechanism for mechanical stop 176 can be provided.

Figure 19:
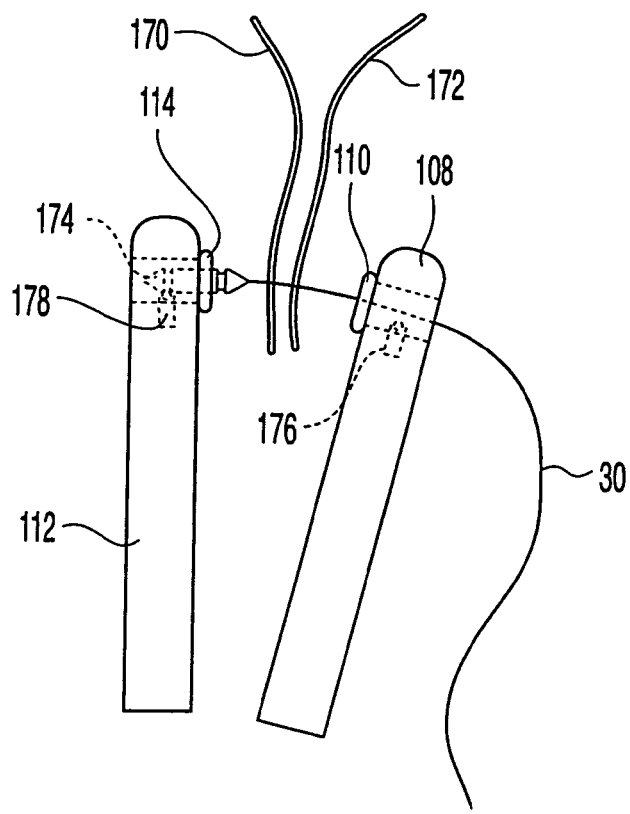
FIG. 19 shows the jaws of FIG. 18 with the implant passed once through the tissue.
Figure 20:
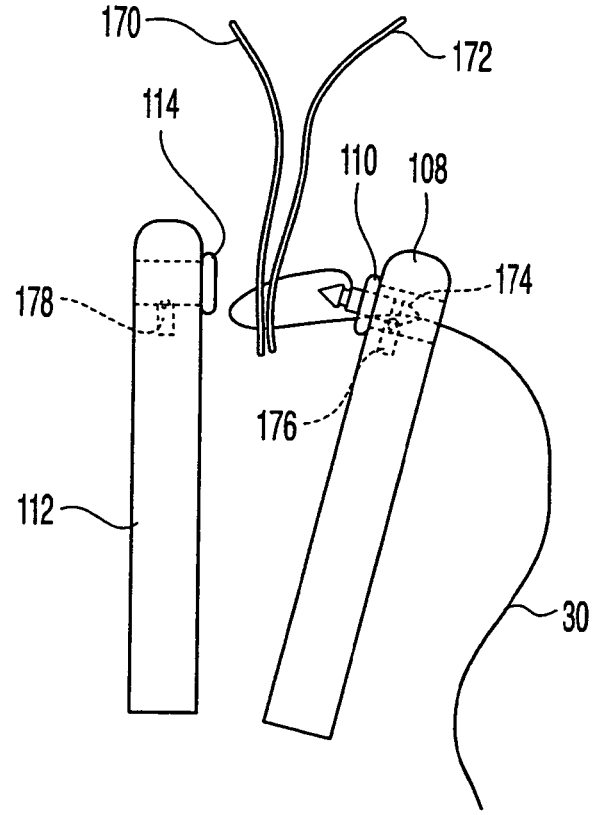
FIG. 20 shows the jaws of FIG. 18 with the implant passed twice through the tissue.

When first and second jaws 108, 112 are properly positioned, first magnetic element 110 is deactivated and second magnetic element 114 is activated to pass implant 174 through tissue sections 170, 172 as shown in FIG. 19. Although the magnetic interaction between second magnetic element 114 and implant 174 may be sufficient to secure implant 174 to second jaw 112, second jaw 112 can be provided with a mechanical stop 178 (also shown as a ball detent mechanism) to further secure implant 174 to second jaw 112. Mechanical stop 178 can also be configured to activate when second magnetic element 114 is activated, or a separate triggering mechanism for mechanical stop 178 can be provided. With implant 174 secured to second jaw 112, first and second jaws 108, 112 can be moved to draw suture 30 tautly through tissue sections 170, 172. This process brings tissue sections 170, 172 into apposition. As shown in FIG. 20, the process of alternating the activation and deactivation of first and second magnetic elements 110, 114 can be repeated as desired to move implant 174 back and forth across tissue sections 170, 172, resulting in suturing of tissue sections 170, 172. As illustrated with respect to the other embodiments, other manipulations of implant 174 and suture 30 are possible with the present invention.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed:

1. A medical system for connecting tissue in a patient, comprising:
   a medical instrument having a distal portion comprising a first jaw and a second jaw pivotably coupled at a pivot point, the first jaw having a first magnetic element and the second jaw having a second magnetic element, wherein the distal portion of the medical instrument is configured to clamp onto at least a one tissue portion when at least one of the first magnetic element and the second magnetic element is activated to generate a magnetic field, wherein the magnetic field is configured to be of sufficient strength to magnetically retain the first jaw and the second jaw in a closed position; and
   a medical implement configured to be removably secured in a mechanical retaining feature in at least one of the first jaw and second jaw, the medical implement configured to be passed from a first side of the at least one tissue portion to a second side of the at least one tissue portion when the first jaw and the second jaw are magnetically retained in the closed position.

2. The medical system of claim 1, wherein the magnetic element of the first jaw of the medical instrument is at least one of a magnetizable material and a permanent magnet, and the magnetic element of the second jaw of the medical instrument is an electromagnet.

3. The medical system of claim 1, wherein the magnetic element of the first jaw of the medical instrument is an electromagnet, and the magnetic element of the second jaw of the medical instrument is least one of a magnetizable material and a permanent magnet.

4. The medical system of claim 1, wherein the medical implement is configured be passed from at least one of the first jaw of the medical instrument to the second jaw of the medical instrument and the second jaw of the medical instrument to the first jaw of the medical instrument when the first jaw and the second jaw are magnetically retained in the closed position.

5. The medical system of claim 4, wherein both the first jaw of the medical instrument and the second jaw of the medical instrument are configured to have a mechanical retaining feature configured to secure the medical implement.

6. The medical system of claim 1, wherein the medical implement is comprised of at least one of polylactic acid, polyglycolic acid, or combinations thereof.

7. The medical system of claim 1, wherein the medical implement is comprised of a non-magnetic material.

8. The medical system of claim 1, wherein the medical implement is configured to affix to the at least one tissue portion in the body of the patient.

9. The medical system of claim 1, further comprising a suture attached to the medical implement.

10. The medical system of claim 1, wherein the medical implement is a suture anchor.

11. The medical system of claim 1, wherein the medical implement is a surgical needle.

12. The medical system of claim 1, further comprising a magnetic field generator configured to be attached to the medical instrument.

* * * * *